(12) United States Patent
Wenzel

(10) Patent No.: US 7,949,397 B1
(45) Date of Patent: May 24, 2011

(54) IMPLANTABLE MEDICAL DEVICE CAPABLE OF DEPRESSING APPETITE TO CONTROL OBESITY USING STOCHASTIC RESONANCE ELECTRICAL STIMULATION

(75) Inventor: Brian Jeffrey Wenzel, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 236 days.

(21) Appl. No.: 11/927,058

(22) Filed: Oct. 29, 2007

(51) Int. Cl.
*A61N 1/18* (2006.01)
(52) U.S. Cl. ......................................................... 607/40
(58) Field of Classification Search .................... 607/40
See application file for complete search history.

(56) References Cited

U.S. PATENT DOCUMENTS

| | | | | |
|---|---|---|---|---|
| 5,836,994 | A * | 11/1998 | Bourgeois ....................... | 607/40 |
| 2003/0018367 | A1 | 1/2003 | DiLorenzo | |
| 2003/0113880 | A1 | 6/2003 | Takenaka et al. | |
| 2004/0243182 | A1* | 12/2004 | Cohen et al. ....................... | 607/2 |
| 2005/0131487 | A1 | 6/2005 | Boveja et al. | |
| 2007/0027486 | A1* | 2/2007 | Armstrong ........................ | 607/2 |

FOREIGN PATENT DOCUMENTS

EP 1537893 6/2005

OTHER PUBLICATIONS

Collins et al., "Noise Mediated Enhancements and Decrements in Human Tactile Sensation", Physical Review E., vol. 56, No. 1, Jul. 1997, 4 pages.
Collins et al., "Noise-Enhanced Information Transmission in Rat SA1 Cutaneous Mechanoreceptors via Aperiodic Stochastic Resonance", Journal of Neurophysiology, vol. 76, No. 1, Jul. 1996, 4 pages.
Kosko et al., "Stochastic Resonance in Noisy Threshold Neurons", Neural Networks 16 (2003) 755-761.
Richardson et al., "Using Electrical Noise to Enhance the Ability of Humans to Detect Subthreshold Mechanical Cutaneous Stimuli", Chaos, vol. 8, Num. 3, Sep. 1998, 5 pages.
Simonotto et al., "Visual perception of Stochastic Resonance", Physical Review letters, vol. 78, Num. 6, Feb. 10, 1997, 4 pages.
Abstract—Fallon et al., "Fully Tuneable Stochastic Resonance in Cutaneous Receptors", J Neurophysiol. Aug. 2005;9492):928-33. Epub Mar. 23, 2005.
Fallon et al., "Stochastic Resonance in Muscle Receptors", J Neurophysiol 91: 2429-2436, 2004.
Abstract—Plesser et al., "Stochastic Resonance in Neuron Models: Endogenous Stimulation Revisited", Phys Rev E Stat Nonlin Soft Matter Phys. Mar. 2001;63(3Pt 1):031916. Epub Feb. 27, 2001.

\* cited by examiner

*Primary Examiner* — Carl H Layno
*Assistant Examiner* — Jeremiah T Kimball
(74) *Attorney, Agent, or Firm* — Theresa Takeuchi; Steven M. Mitchell

(57) ABSTRACT

Methods and devices are provided for influencing an amount of food ingested. The methods include applying stochastic resonance stimulation to a stomach to influence a nervous system response using an implantable stimulation device. In one embodiment, a device includes electrodes in communication with a gastric wall capable of delivering stimulation therapy, and a controller adapted to apply stochastic resonance stimulation to a stomach to influence a response of stomach receptors and/or interstitial cells of Cajal. In some embodiments, the implantable device is configured to apply a suprathreshold signal in addition to the stochastic resonance stimulation. In some embodiments, the implantable device is configured to apply an electrical signal in other areas of the nervous system besides the stomach. In some embodiments, the implantable stimulation device is an implantable cardiac stimulation device capable of providing therapy to a heart.

23 Claims, 4 Drawing Sheets

IMPLANTABLE MEDICAL DEVICE CAPABLE OF DEPRESSING APPETITE TO CONTROL OBESITY USING STOCHASTIC RESONANCE ELECTRICAL STIMULATION

BACKGROUND

Obesity is a growing epidemic in the United States. Currently, more than 15% of the population is obese. Obesity is characterized by a body mass index (BMI) greater than 30.0 kg/m$^2$. Many diseases, including stroke, diabetes mellitus, and cardiovascular disease, have obesity as a substantial risk factor. The need to develop better methods of treatment has increased now more than ever. Current treatments involve surgical interventions that reshape the gastrointestinal tracks. These procedures have a high mortality rate and often lead to other complications such as malnutrition.

In other approaches, the stomach or the nerves to the stomach are electrically stimulated to create a sensation of fullness, to cause individuals to stop eating at an earlier point than normal, which will cause the individual to cut caloric intake. Recent studies have shown that the electrical stimulation of the vagal afferent nerves reduces food intake in laboratory animals which leads to a significant weight loss. Selective electrical stimulation of the afferent nerve fibers from the stomach, however, is difficult. Also, non-selective electrical stimulation could reduce the effectiveness of the treatment.

What is needed is a device and method to safely control food intake. Further what is needed is an implantable device capable of influencing food intake.

SUMMARY

In one implementation, a method is provided for influencing an amount of food ingested. The method includes applying stochastic resonance stimulation to the stomach to influence a nervous system response using an implantable stimulation device.

In one embodiment, an implantable stimulation device is provided which is capable of influencing food intake. The device including electrodes in communication with a gastric wall capable of delivering stimulation therapy, and a controller adapted to apply stochastic resonance stimulation to the stomach to influence a nervous system response. In some embodiments, the implantable stimulation device is an implantable cardiac stimulation device capable of also providing therapy to a heart.

BRIEF DESCRIPTION OF THE DRAWINGS

Further features and advantages of the invention may be more readily understood by reference to the following description taken in conjunction with the accompanying drawings, in which.

DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview of Intracardiac Stimulation Device

Figure 1:
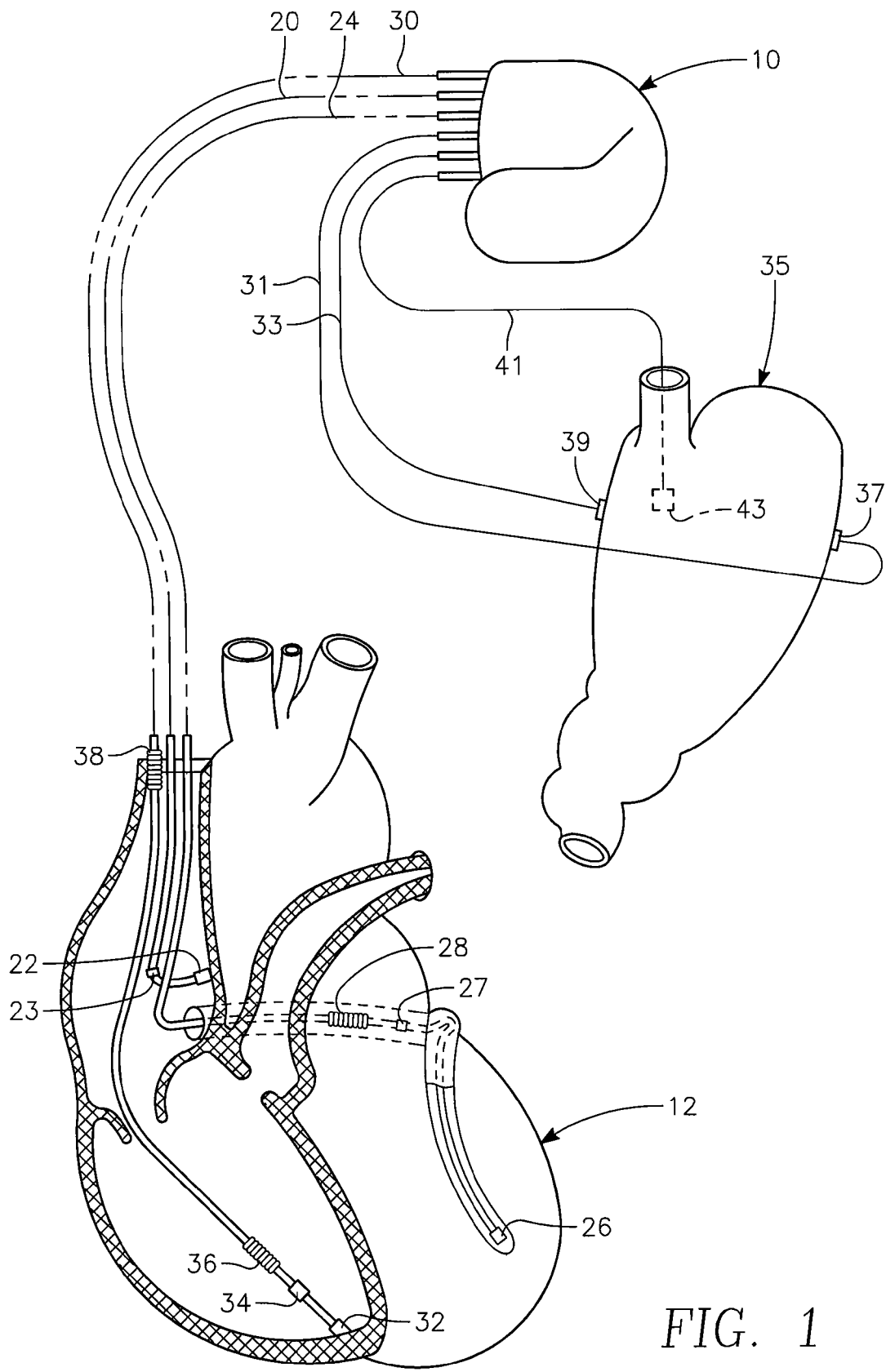
FIG. 1 illustrates a stimulation device in electrical communication with a patient's heart.

FIG. 1 illustrates a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, in some embodiments, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
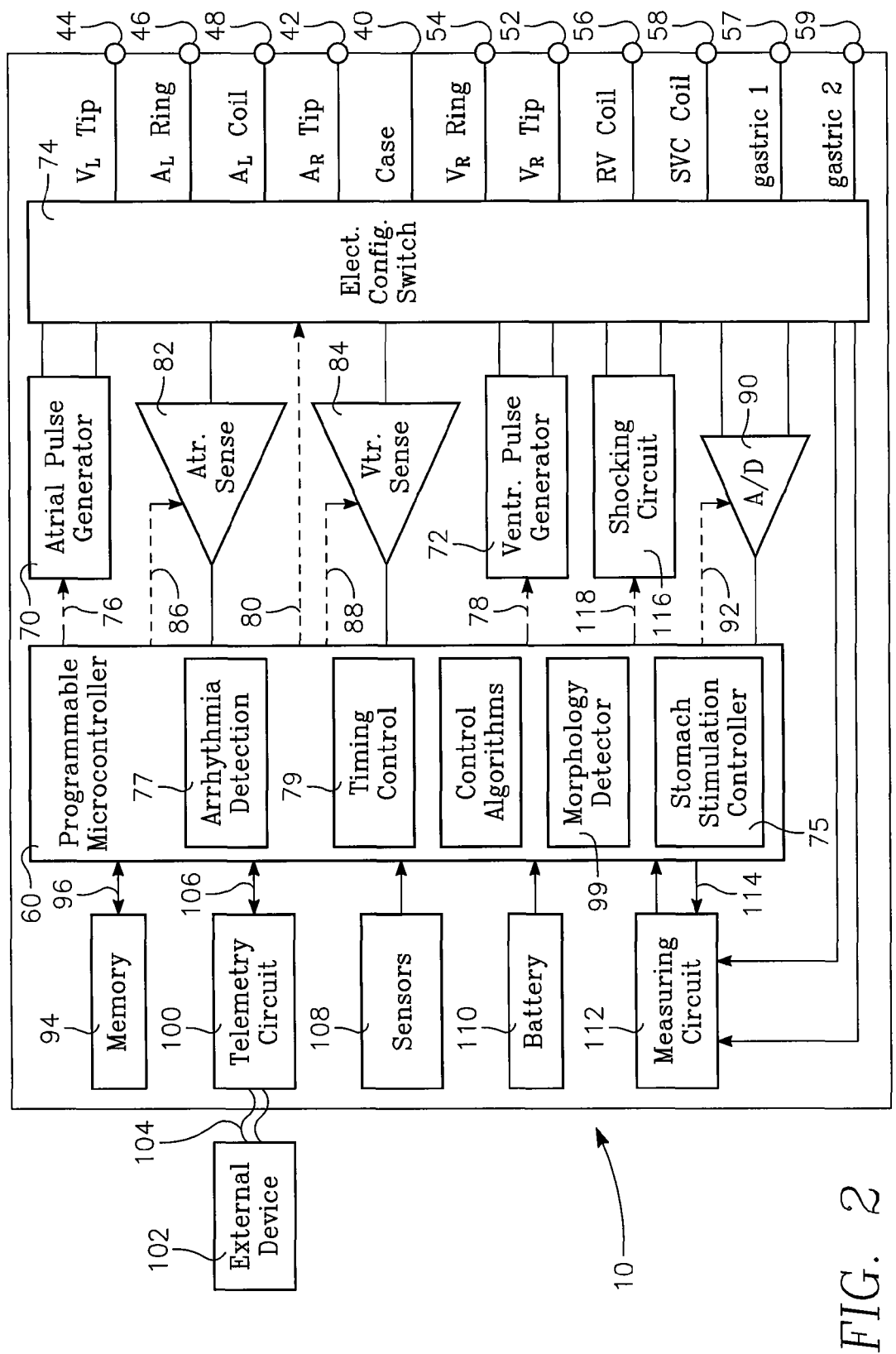
FIG. 2 illustrates a simplified block diagram of the stimulation device in accordance with one embodiment.

FIG. 2 illustrates a simplified block diagram of the stimulation device 10 in accordance with one embodiment of the present invention. The stimulation device 10 is capable of treating both fast and slow arrhythmias with stimulation therapy, including cardioversion, defibrillation, and pacing stimulation. While a particular stimulation device 10 is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40. The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode individually or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) terminal 46 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, the right ventricular ring electrode 34, the right ventricular coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator (Vtr. Pulse Generator) 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes a timing control circuit 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

In one embodiment, the stimulation device 10 may include an atrial sensing circuit (Atr. Sense) 82 and a ventricular sensing circuit (Vtr. Sense) 84. The atrial sensing circuit 82 and ventricular sensing circuit 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial sensing circuit 82 and ventricular sensing circuit 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, may employ one or more low power, precision amplifiers with programmable gain and/or automatic gain control, bandpass filtering, and a threshold detection circuit, as known in the art, to selectively sense the cardiac signal of interest. The bandpass filtering may include a bandpass filter that passes frequencies between 10 and 70 Hertz (Hz) and rejects frequencies below 10 Hz or above 70 Hz. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 may utilize the atrial and ventricular sensing circuits 82 and 84 to sense cardiac signals to determine whether a rhythm is physiologic or pathologic. The timing intervals between sensed events (e.g., P-waves, R-waves, and depolarization events associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

In another embodiment, the stimulation device 10 may include an analog-to-digital (A/D) data acquisition circuit 90. The data acquisition circuit 90 is configured to acquire an intracardiac signal, convert the raw analog data of the intracardiac signal into a digital signal, and store the digital signals for later processing and/or telemetric transmission to an external device 102. The data acquisition circuit 90 is coupled to the right atrial lead 20, the coronary sinus lead 24, and the right ventricular lead 30 through the switch 74 to sample cardiac signals across any pair of desired electrodes. As shown in FIG. 2 the microcontroller 60 generates a control signal 92 to control operation of the data acquisition circuit 90.

The microcontroller 60 includes an arrhythmia detector 77, which operates to detect an arrhythmia, such as tachycardia and fibrillation, based on the intracardiac signal. The arrhythmia detector 77 senses R-waves in the intracardiac signal, each of which indicates a depolarization event occurring in the heart 12. The arrhythmia detector 77 may sense an R-wave by comparing a voltage amplitude of the intracardiac signal with a voltage threshold value. If the voltage amplitude of the intracardiac signal exceeds the voltage threshold value, the arrhythmia detector 77 senses the R-wave. The arrhythmia detector 77 may also determine an event time for the R-wave occurring at a peak voltage amplitude of the R-wave. The arrhythmia detector 77 may receive an analog intracardiac signal from the sensing circuits 82 and 84 or a digital intracardiac signal from the data acquisition circuit 90. Alternatively, the arrhythmia detector 77 may use the digitized intracardiac signal stored by the data acquisition circuit 90.

In one embodiment, the microcontroller 60 includes a morphology detector 99 for confirming R-waves. The morphology detector 99 compares portions of the intracardiac signal with templates of known R-waves to confirm R-waves sensed in the intracardiac signal. In various embodiments, the morphology detector 99 is optional.

The microcontroller 60 is further coupled to a memory 94 by a suitable computer bus 96 (e.g., an address and data bus), wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. (V-V delay is typically used only in connection with independently programmable RV and LV leads for biventricular pacing.) While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 should be capable of operating at low current drains for long periods of time, and then be capable of providing high-current pulses (for capacitor charging) when the patient requires a shock pulse. The battery 110 should also have a predictable discharge characteristic so that elective replacement time can be detected. Accordingly, the stimulation device 10 may employ lithium/silver vanadium oxide batteries. As further shown in FIG. 2, the stimulation device 10 is shown as having a measuring circuit 112 which is enabled by the microcontroller 60 via a control signal 114.

In the case where the stimulation device 10 is intended to operate as an implantable cardioverter/defibrillator (ICD) device, the stimulation device 10 detects and confirms the occurrence of an arrhythmia, and automatically applies an appropriate antitachycardia pacing therapy or electrical shock therapy to the heart 12 for terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and/or the SVC coil electrode 38. As noted above, the housing 40 may act as an active electrode in combination with the right ventricular coil electrode 36, or as part of a split electrical vector using the SVC coil electrode 38 or the left atrial coil electrode 28 (i.e., using the right ventricular coil electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 5 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Stochastic Resonance Electrical Stimulation

Methods and devices for influencing an amount of food ingested are provided. In one embodiment, the method includes applying stochastic resonance stimulation to the stomach to influence a nervous system response using an implantable stimulation device.

In one embodiment, the actual receptors in the stomach are activated. The receptors then detect the stimulation and transmit this signal along the nerve. In various embodiments, stochastic resonance is introduced to change the gain of the receptors. In one embodiment, stochastic resonance stimulation is applied to interstitial cells of Cajal (ICC) of the stomach.

Stochastic resonance is the practice of adding noise to a system to increase the system's signal to noise ratio. Stochastic resonance may increase the gain of the receptors by introducing signals in the form of noise, so that the receptors send out modified information regarding the fullness of the stomach. The receptors are activated in such a way that when the stomach is half full, for example, the receptors respond as though the stomach is completely full. An individual with this system would feel satiated sooner which leads to the reduction of calorie intact. Thus, in some implementations, stochastic resonance electrical stimulation of the stomach's nerve fibers may be used to treat obesity.

Stochastic resonance electrical stimulation, applied directly to the stomach activates at least one of two mechanisms to cause weight loss. First, stochastic resonance stimulation decreases the threshold for action potential initiation in stretch receptors located within the stomach wall such that the sensation of "fullness" will be achieved at a lower food intake, leading to weight loss.

With the second mechanism, stochastic resonance stimulation decreases the threshold of the interstitial cells of Cajal (ICC) within the plexus, allowing for larger and more frequent peristaltic contractions. The interstitial cells of Cajal are a plexus of neurons within the stomach, which depolarize in a rhythmic pattern. They are critical in slow wave generation, which creates the peristaltic stomach contractions. These slow wave contractions are used to grind the food and to push the food to the duodenum. Stochastic resonance stimulation may be used to accelerate movement of food through the stomach, thereby decreasing the amount of food digested and leading to lower calorie absorption in the intestine.

Stochastic resonance stimulation of the interstitial cells of Cajal in the stomach wall can create weight loss by changing the peristaltic stomach contractions without the complications of selective stimulation as with vagal stimulation or the side effects associated with vagal nerve stimulation.

As shown in FIG. 1, the implantable stimulation device 10 described herein can be a pacemaker or a defibrillator plus pacemaker, with all the standard components of such devices. Furthermore, the implantable stimulation device 10 may include a specialized stomach stimulation controller 75 (shown in FIG. 2) which provides signals via terminals 57 and 59 to multi-electrode leads 31 and 33 capable of electrically stimulating/inhibiting the electrical activity of the stomach 35.

The stomach stimulation controller 75 may be included in the programmable microcontroller 60 as shown in FIG. 2, or be a separate control unit within the implantable stimulation device 10, or integrated with the cardiac functions. Moreover, in other embodiments (not shown), a separate implantable gastric/stomach stimulator may be utilized.

Electrodes 37 and 39, or more, are placed around the stomach to optimize the electrical field around the stretch receptors and/or the ICC. In one embodiment, electrodes are placed at other locations of the peripheral nervous system as well. In one embodiment, electrodes are also placed in contact with the central nervous system, such as along the spinal cord. (The position and number of electrodes is simplified in FIG. 1 for illustration purposes.) The stimulation amplitudes, frequencies, burst lengths, burst frequencies, and stimulation type may be adjusted to match the person's weight loss needs.

The electrical stimulation types may be stochastic resonance, electrical stimulation less than about 150 Hz, and electrical stimulation greater than about 150 Hz. Different electric stimulation types, amplitudes, frequency, and pulse width may be applied via different electrodes. The stochastic resonance electrical stimulation will have an amplitude below a threshold for creating an action potential and is used to generate action potentials by depolarizing stretch receptors and the ICC without depolarizing axons of passage. An electrical stimulation less than about 150 Hz will have an amplitude large enough to generate action potentials by depolarizing axons of passage, thereby providing an artificial signal to the nervous system indicating satiation. An electrical stimulation greater than about 150 Hz will be a suprathreshold electrical signal that may block the propagation of action potentials that would otherwise indicate satiation. In other embodiments, frequencies less than about 200 Hz, and/or greater than about 200 Hz could be used, depending upon where along the nervous system electrodes are placed. In yet other embodiments, lower or higher frequency electrical stimulation may be used.

For each type of electrical stimulation, the waveform could be monophasic, biphasic, and/or multiphasic rectangular, sinusoidal, and/or trapezoidal shape; have an amplitude ranging from 0 to 50 mA; and a pulse width ranging from 0.025 to 50 ms. The frequency content of the stochastic resonance electrical stimulation can have a Gaussian distribution, binomial distribution, uniform distribution, non-uniform distribution, and/or be skewed towards any frequency or set of frequencies. In one embodiment, the majority of the power in the stochastic resonance electrical stimulation is below 2000 Hz. In one embodiment, about 95% of the power of the electrical stimulation is less than about 2000 Hz. In one embodiment, all of the power in the stochastic resonance electrical stimulation is below 2000 Hz.

The programmable microcontroller 60 (or other programmable processing unit) can be programmed to deliver stomach stimulation with predefined parameters (amplitude, frequency, and pulse width) for a specified amount of time (periodic or continuous) based on a preset pattern or developed based on the individual's weight loss needs. Additionally, the device may be equipped with pressure monitoring sensor(s) 43 within the stomach 35 such that the micorocontroller 60, or other processor, can process pressure measurements and use that information to adjust the amplitude, frequency, pulse width, and type of the nerve stimulation based on eating and drinking patterns. The pressure monitoring sensor(s) 43 may have separate lead(s) 41 and/or sensor(s), or be integrated with the leads 31 and 33 and electrodes 37 and 39.

The system may also have an activity sensor. The activity sensor can monitor a person's daily activity to determine the amount of food necessary for that day. For instance, if a person exercises a lot one day, the system will adjust the amplitude, frequency, pulse width, and type of the nerve stimulation such that the person can consume more food.

Figure 3:
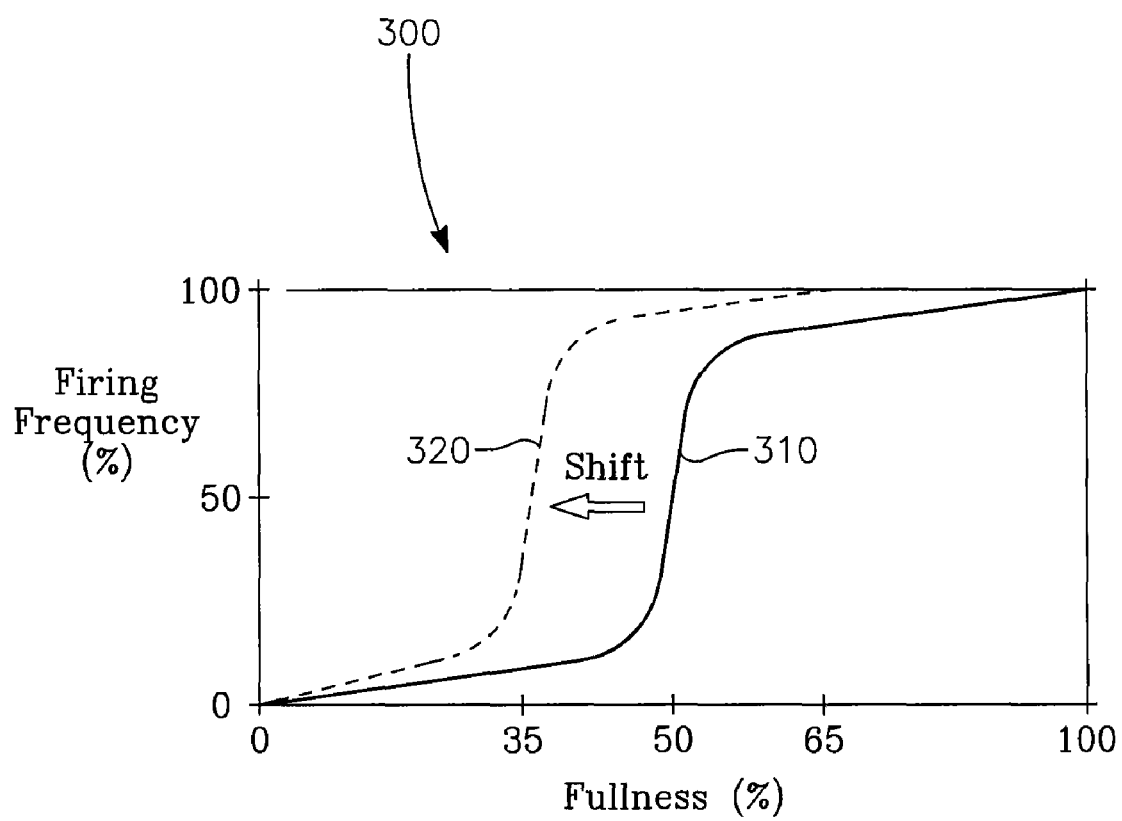
FIG. 3 illustrates a response curve of a stomach receptor.

FIG. 3 illustrates a response curve 300 of a receptor. Shown in FIG. 3, in a normal response curve 310, as the fullness of the stomach increases, the firing frequency of the receptors increases with a sigmoidal relationship. In general, when the stomach is 100% full the firing frequency of the receptors is at 100%. Introduction of stochastic resonance to the stomach causes the curve 310 to shift to the left as illustrated by curve 320. So, in this example, instead of needing to reach 50% fullness to produce a 50% firing frequency, 35% fullness on curve 320 will provide 50% firing frequency response. Thus the shift in the response curve shown in FIG. 3, produces a greater firing frequency for less actual fullness. Since a greater firing frequency corresponds with greater satiation, a less than full stomach can provide a sensation of fullness with the utilization of stochastic resonance.

Figure 4:
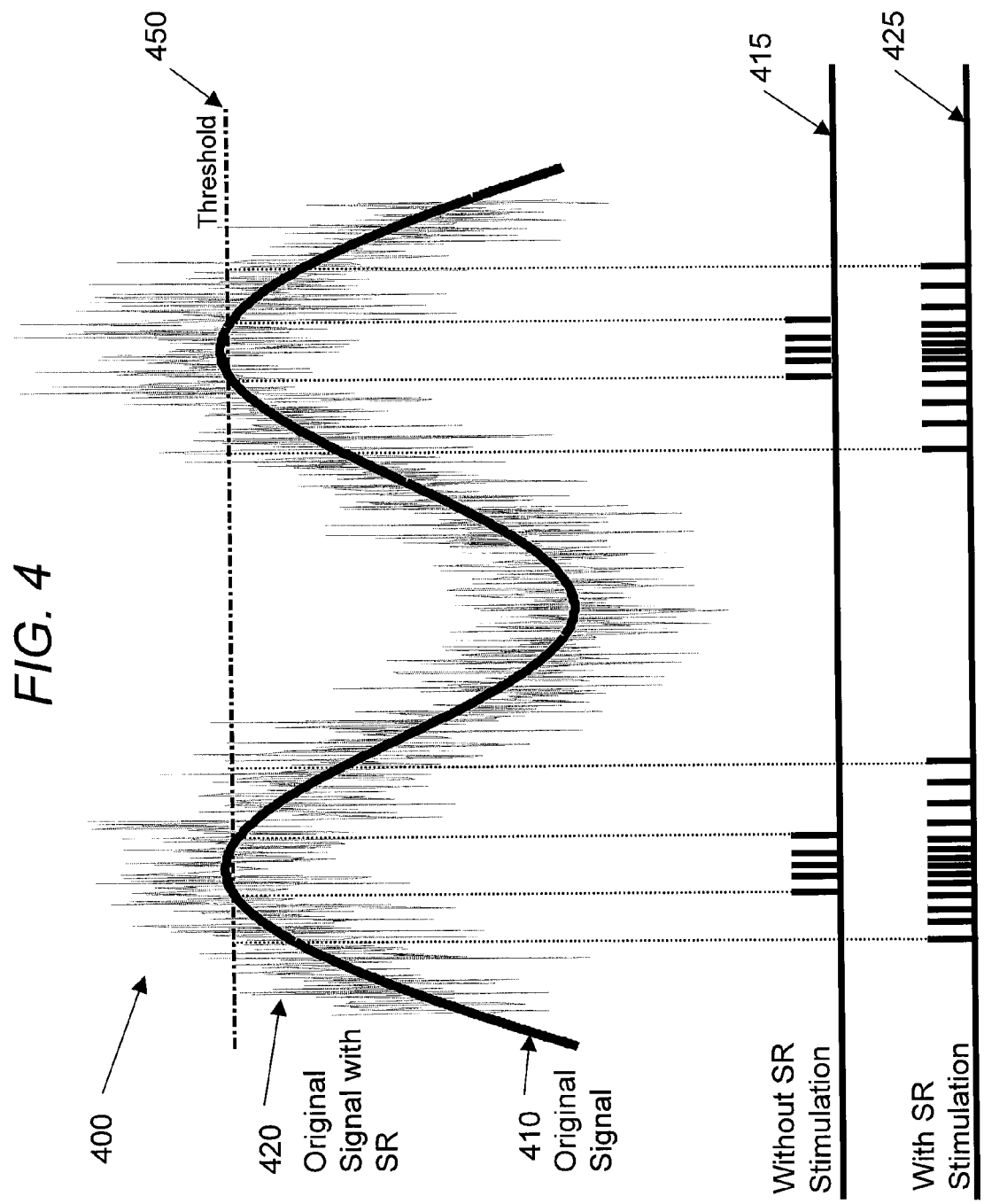
FIG. 4 is a plot illustrating an example of the effect of introducing noise to the receptors.

FIG. 4 is a plot 400 illustrating an example of the effect of introducing noise to the receptors. The receptor firing response 415 without noise corresponds to signal 410 without noise. The signal 410 could represent the amount of food and drink in the stomach. As the amount increases, the receptor generates action potentials. When the stomach contents decrease, the receptor stops firing. The receptor firing response 425 with noise corresponds to the signal 420 with noise. As is shown, the receptors fire for a longer interval with noise because the signal 420 crosses the receptor firing threshold 450 sooner and remains over it longer. The receptors also fire with greater frequency because the magnitude of the signal 420 with noise, reaches a greater magnitude above the receptor firing threshold 450. Thus more of the signal 420 crosses above the receptor firing threshold 450 and has a greater magnitude above the receptor firing threshold 450. In this example, the stochastic resonance added to the signal causes the generation of action potential to occur sooner and last for a longer time interval.

Introducing stochastic resonance electrical noise signals at a subthreshold frequency increases the gain of the receptor, effectively lowering the threshold 450 required for receptor firing.

Although the implantable stimulation device is shown and described above as also containing cardiac stimulation capability, not all embodiments contain of the implantable stimulation device contain cardiac capability.

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method for influencing an amount of food ingested, the method comprising applying stochastic resonance electrical stimulation directly to a surface of a stomach using electrodes implanted on the surface of the stomach, wherein the stochastic resonance electrical stimulation has an amplitude in a range from greater than about 0 mA to about 50 mA, wherein the stochastic resonance electrical stimulation has an amplitude below a threshold for depolarizing axons of passage of vagal nerves innervating the stomach, and wherein the stochastic resonance electrical stimulation has an amplitude sufficient to decrease the threshold for action potential initiation in stretch receptors of the stomach.

2. The method of claim 1, wherein applying stochastic resonance electrical stimulation comprises stimulating stretch receptors.

3. The method of claim 1, wherein applying stochastic resonance electrical stimulation comprises stimulating interstitial cells of Cajal and wherein the stochastic resonance electrical stimulation has an amplitude sufficient to decrease the threshold of interstitial cells of Cajal.

4. The method of claim 1, wherein at least about 95% of the power of the stochastic resonance electrical stimulation is less than 2000 Hz.

5. The method of claim 1, further comprising applying a second electrical stimulation to the surface of the stomach using the implantable stimulation device, wherein the second electrical stimulation has an amplitude between 0 to 50 mA, wherein the second electrical stimulation is less than 150 Hz and has an amplitude effective to generate action potentials by depolarizing axons of passage.

6. The method of claim 1, further comprising applying a second electrical stimulation to the surface of the stomach using the implantable stimulation device, wherein the second electrical stimulation has an amplitude between 0 to 50 mA, wherein the second electrical stimulation is greater than 150 Hz and has an amplitude effective to block the propagation of action potentials by depolarizing axons of passage.

7. The method of claim 1, wherein a frequency distribution of the stochastic resonance electrical stimulation represents a Gaussian distribution, a binomial distribution, a uniform distribution, or a non-uniform distribution.

8. The method of claim 1 further comprising monitoring a pressure associated with the stomach and adjusting at least one of: (a) an amplitude; (b) a frequency, (c) a pulse width, or (d) a stimulation type of the stochastic resonance electrical stimulation based on the pressure.

9. The method of claim 1 further comprising monitoring an activity of an individual and adjusting at least one of: (a) an amplitude; (b) a frequency, (c) a pulse width, or (d) a stimulation type of the stochastic resonance electrical stimulation based on the activity of the individual.

10. The method of claim 1 further comprising applying a suprathreshold electrical stimulation to the surface of the stomach having a waveform that is at least one of: (a) monophasic rectangular; (b) biphasic rectangular, or (c) multiphasic rectangular; (d) sinusoidal, or (e) trapezoidal shape.

11. The method of claim 1 further comprising applying a suprathreshold electrical stimulation to the surface of the stomach having a waveform having a pulse width in a range from about 0.025 to about 50 milliseconds.

12. An implantable stimulation device capable of influencing food intake, the device comprising:
electrodes in communication with a surface of a gastric wall so as to be capable of delivering stimulation therapy to the gastric wall; and
a controller adapted to apply stochastic resonance stimulation to the electrodes, wherein the stochastic resonance electrical stimulation has an amplitude in a range from greater than about 0 mA to about 50 mA, wherein the stochastic resonance electrical stimulation has an amplitude below a threshold for depolarizing axons of passage of vagal nerves innervating the stomach, and wherein the stochastic resonance electrical stimulation has an amplitude sufficient to decrease the threshold for action potential initiation in stretch receptors of the stomach.

13. The device of claim 12, wherein the implantable stimulation device is an implantable cardiac stimulation device capable of providing therapy to a heart.

14. The device of claim 12, wherein the controller is adapted to apply stochastic resonance stimulation to stretch receptors.

15. The device of claim 12, wherein the controller is adapted to apply stochastic resonance stimulation to interstitial cells of Cajal.

16. The device of claim 12, wherein at least about 95% of the power of the stochastic resonance stimulation is less than about 2000 Hz.

17. The device of claim 12, wherein the controller is further adapted to provide an electrical stimulation to the electrodes of less than about 150 Hz effective to depolarize axons of passage.

18. The device of claim 12, wherein the controller is further adapted to provide an electrical stimulation of more than about 200 Hz effective to block the propagation of action potentials.

19. The device of claim 12, wherein the stochastic resonance stimulation has a frequency distribution and amplitude that is customized to an individual receiving the stochastic resonance stimulation.

20. The device of claim 12, wherein the stochastic resonance stimulation has a frequency distribution that represents a Gaussian distribution, a binomial distribution, a uniform distribution, or a non-uniform distribution.

21. The device of claim 12, further comprising a pressure sensor in communication with the stomach, the controller being further adapted to monitor a pressure associated with the stomach and adjust at least one of: (a) an amplitude; (b) a frequency, (c) a pulse width, or (d) a stimulation type of the stochastic resonance stimulation based on the pressure.

22. The device of claim 12, further comprising an activity sensor in communication with an individual, the controller being further adapted to adjust at least one of: (a) an amplitude; (b) a frequency, (c) a pulse width, or (d) a stimulation type of the stochastic resonance stimulation based on the activity of the individual.

23. The device of claim 12, wherein the controller is further adapted to apply a suprathreshold electrical stimulation waveform comprising a pulse width ranging from about 0.025 to about 50 milliseconds.

* * * * *